United States Patent [19]

Wang

[11] Patent Number: 5,470,998
[45] Date of Patent: Nov. 28, 1995

[54] PROCESS FOR THE PREPARATION OF ESTERS OF STILBENEDICARBOXYLIC ACID

[75] Inventor: Richard H. S. Wang, Kingsport, Tenn.

[73] Assignee: Eastman Chemical Company, Kingsport, Tenn.

[21] Appl. No.: 398,841

[22] Filed: Mar. 6, 1995

[51] Int. Cl.⁶ .................................................. C07C 67/343
[52] U.S. Cl. ................................ 560/96; 562/493; 560/76
[58] Field of Search ......................... 560/96, 76; 562/493

[56] References Cited

U.S. PATENT DOCUMENTS

| | | |
|---|---|---|
| 3,586,673 | 6/1971 | Bloom et al. . |
| 4,713,472 | 12/1987 | Van Sickle .................................. 560/78 |
| 4,789,755 | 12/1988 | Van Sickle .................................. 560/53 |
| 5,113,010 | 5/1992 | Langer et al. . |

OTHER PUBLICATIONS

J. Organic Chemistry, 26, 5243, (1961).
J. Amer. Chem. Soc., 83, 1733, (1961).
"A Practical Approach to Homo Trialkyl Phosphonates", Synthetic Communications, 20(2), 239–246 (1990).
J. Amer. Chem. Soc., 47, 3003, (1925).
J. Amer. Chem. Soc., 61, 2142, (1939).

*Primary Examiner*—José G. Dees
*Assistant Examiner*—Samuel Barts
*Attorney, Agent, or Firm*—J. Frederick Thomsen; Harry J. Gwinnell

[57] ABSTRACT

Disclosed is a process for the preparation of 4,4'-stilbenedicarboxylate esters by a 3-step process utilizing p-toluic acid, an alkyl p-formylbenzoate and a trialkyl phosphite. The steps comprise (1) preparing p-(chloromethyl)benzoic acid by chlorinating p-toluic acid with sulfuryl chloride in the presence of a free radical initiator and chlorobenzene or dichlorobenzene;

(2) contacting the p-(chloromethyl)benzoic acid of step (1) with a trialkyl phosphite to obtain a phosphonate compound; and (3) contacting the phosphonate ester compound of step (2) with an alkyl p-formylbenzoate in the presence of an alkali metal alkoxide and an inert solvent to obtain the dialkyl 4,4'-stilbenedicarboxylate.

9 Claims, No Drawings

PROCESS FOR THE PREPARATION OF ESTERS OF STILBENEDICARBOXYLIC ACID

This invention pertains to a novel process for the preparation of esters of 4,4'-stilbenedicarboxylic acid. More specifically, this invention pertains to a 3-step process for the synthesis of dialkyl esters of 4,4'-stilbenedicarboxylic acid from p-toluic acid and alkyl p-formylbenzoates utilizing intermediate phosphite and phosphonate compounds.

Dialkyl 4,4'-stilbenedicarboxylates and 4,4'-stilbenedicarboxylic acid are used in the manufacture of optical brighteners or whiteners. For example, U.S. Pat. No. 4,921,964 discloses the preparation of bis(2-benzoxazolyl)stilbene compounds by the reaction of dialkyl stilbenedicarboxylate esters with various 2-aminophenol compounds in the presence of certain solvents and catalysts. Optical brighteners are used extensively in synthetic plastics and fibers to improve the appearance, e.g., the apparent whiteness, thereof. The preparation of a mixture of 4,4'-bibenzyldicarboxylic and 4,4'-stilbenedicarboxylic acids by heating a stoichiometric excess of p-toluic acid with sulfur is disclosed in U.S. Pat. No. 2,677,703. The disadvantages involved in this method for producing 4,4'-stilbenedicarboxylic acid include (i) high temperatures in the range of 250° to 290° C. are required, (ii) the product mixture containing the starting material, p-toluic acid, and the 2 products, 4,4'-bibenzyldicarboxylic and 4,4'-stilbenedicarboxylic acids, are very difficult to separate, (iii) the low yields, e.g., 40% at best, obtained, and (iv) the necessity to prevent the hydrogen sulfide produced from escaping by costly scrubbing procedures.

It also is known to heat a stoichiometric excess of p-toluic acid with sulfur at 265° C. at a pressure of about 5.5 bars absolute in the presence of nitrogen to obtain 4,4'-stilbenedicarboxylic acid in a 34% yield based on the amount of sulfur used. A known method for synthesizing dimethyl 4,4'-stilbenedicarboxylate comprises the steps of (1) contacting methyl p-formylbenzoate with hydrogen sulfide at 0° C. in the presence of hydrochloric acid to produce a cyclic trisulfide compound and (2) heating the cyclic trisulfide compound at 220° to 260° C. in the presence of copper and diphenyl ether. Dimethyl 4,4'-stilbenedicarboxylate is obtained in an overall yield, based on the methyl p-formylbenzoate starting material, of 37.5%. Both of these methods, like the process of U.S. Pat. No. 2,677,703, produce hydrogen sulfide and, thus, require special equipment to treat the process effluent. These processes require the use of special, dedicated equipment and are not well suited for use in general purpose equipment. Additional methods for preparing stilbene compounds are described by K. B. Becker, Synthesis of Stilbenes, Synthesis, May 1983, 341–368 and U.S. Pat. No. 5,113,010.

I have developed a process which does not require the use of sulfur and may be operated at moderate process conditions in general purpose, chemical manufacturing equipment. The process of the present invention provides a novel method for producing a dialkyl ester of 4,4'-stilbenedicarboxylic acid having the formula

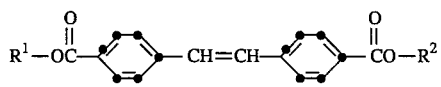

by the steps comprising:

(1) preparing p-(chloromethyl)benzoic acid by chlorinating p-toluic acid with sulfuryl chloride in the presence of a free radical initiator and chlorobenzene or dichlorobenzene;

(2) contacting the p-(chloromethyl)benzoic acid of step (1) with a trialkyl phosphite having the formula $(R^2O)_3P$ to obtain a phosphonate compound having the formula:

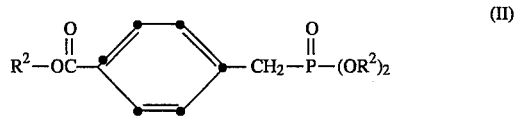

and (3) contacting the phosphonate ester compound of step (2) with an alkyl p-formylbenzoate in the presence of an alkali metal alkoxide and an inert solvent to obtain the dialkyl 4,4'-stilbenedicarboxylate;

wherein $R^1$ is alkyl of 1 to 6 carbon atoms and $R^2$ is alkyl of 2 to 6 carbon atoms. The 3-step process may be operated in general purpose equipment in which steps (2) and (3) may be carried out in the same reactor.

The first step of the process is carried out in chlorination equipment wherein p-toluic acid is contacted with sulfuryl chloride in the presence of a free radical initiator and chlorobenzene and/or dichlorobenzene to convert the p-toluic acid to p-(chloromethyl)benzoic acid (or α-chlorotoluic acid). This chlorination procedure is carried out at a temperature of about 70° to 100° C. at ambient or autogenous pressure using at least 1, and preferable 1.1 to 2 moles of sulfuryl chloride per mole of p-toluic acid. The free radical initiator may be selected from various peroxides such as aroyl peroxides, e.g., benzoyl peroxide, and azo compounds such as 2,2'-azobisisobutyrnitrile and 1,1-azobis(cyclohexanecarbonitrile). The amount of free radical initiator employed typically is in the range of about 0.01 to 0.10 moles initiator per mole of p-toluic acid. The use of chlorobenzene, dichlorobenzene or a mixture thereof as the process solvent produces an unexpected benefit in that the desired product, p-(chloromethyl)benzoic acid, is essentially insoluble in chlorobenzene and dichlorobenzene. Thus, as p-(chloromethyl)benzoic acid forms during the chlorination step, it precipitates and formation of dichlorinated material, p-(dichloromethyl)-benzoic acid, is minimized. Accordingly, step (1) of the process defined above constitutes a separate embodiment of the present invention. The weight ratio of chlorobenzene and/or dichlorobenzene solvent employed to the p-toluic acid starting material normally is about 1:1 to 5:1, preferably about 2:1 to 4:1. The p-(chloromethyl)benzoic acid obtained from step (1) is isolated by filtration, normally washed to remove residual sulfuryl chloride and initiator and used in step (2) without further purification.

Step (2) is carried out by simply heating a mixture of the p-(chloromethyl)benzoic acid from step (1) and a trialkyl phosphite at a temperature of about 140 to 180° C. Step (2) conveniently is performed using an excess of the trialkyl phosphite as the reaction solvent or medium. For example, the mole ratio of trialkyl phosphite to the p-(chloromethyl)benzoic acid may be in the range of about 2:1 to 10:1, preferably in the range of about 3:1 to 5:1. Upon completion of step (2), the excess (unreacted) trialkyl phosphite normally is removed from the product by distillation. During the course of the reaction of step (2), the toluic acid carboxyl group is esterified with an alkyl group derived from the phosphite ester $(R^2O)_3P$. This esterification inherent in step (2) results in the formation of a stilbenedicarboxylic acid diester rather than a monoester.

The third step of the process of the present invention comprises contacting the phosphonate ester compound of step (2) with an alkyl p-formylbenzoate having the structure

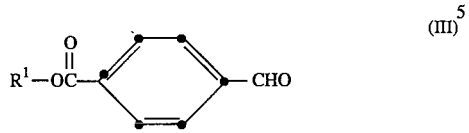

in the presence of an alkali metal alkoxide and an inert solvent to obtain the dialkyl 4,4'-stilbenedicarboxylate. Examples of the alkali metal alkoxides which may be used in step (3) include the sodium, potassium, lithium and cesium alkoxides containing 1 to 4 carbon atoms. The amount of alkali metal alkoxide used typically is at least one mole alkali metal alkoxide per mole of alkyl p-formylbenzoate, preferably about 1.2 to 2.0 moles alkali metal hydroxide per mole of alkyl p-formylbenzoate. Step (3) typically is carried out at a temperature of about 25° to 35° C. in the presence of an inert, polar, aprotic solvent. Inert solvents which may be used include dimethylformamide, dimethylacetamide, dimethylsulfoxide, glycol diethers, glycol diesters, glycol ether esters and haloaromatic compounds.

With reference to step (1), the chlorination of toluene using sulfuryl chloride and benzoyl peroxide is disclosed by Kharasch et al., J. Amer. Chem. Soc., 61, 2442 (1939). However, Case, J. Am. Chem. Soc., 47, 3003 (1925) teaches the preparation of p-(chloromethyl)benzoic acid by heating p-cyanobenzyl chloride with concentrated hydrochloric acid for 10 hours. With reference to steps (2) and (3) the reaction of (i) α-bromotoluic acid and triethyl phosphite to produce diethyl p-carboxybenzylphosphonate and (ii) diethyl p-carboxybenzylphosphonate with p-(2-benzoxazolyl)benzaldehyde in the presence of DMSO and sodium methoxide to produce 4-(2'-benzoxazolyl)-4'-stilbenecarboxylic acid is described in Example 22 of U.S. Pat. No. 3,586,673. Seus et al., Journal of Organic Chemistry, 26, 5243 (1961) describe the preparation of stilbene and heterocyclic analogs by heating a mixture of diethyl benzylphosphonate, benzaldehyde or a heterocyclic carboxaldehyde, sodium methoxide and dimethylformamide. The novelty and inventive merit of the present process is predicated primarily on the unique combination of steps which require a minimum use of general purpose equipment to operate on a commercial scale. For example, steps (2) and (3) can be conveniently and economically carried out in the same reaction vessel.

The process of the present invention is further illustrated by the following examples.

STEP (1)

A solution of p-toluic acid (27.2 g, 0.2 mole) in chlorobenzene is heated to 90° C. in a 250-mL, 3-neck flask equipped with 2 dropping funnels for the addition of the initiator and the sulfuryl chloride. A solution of 1,1-azobis-(cyclohexanecarbonitrile) (0.75 g) in 25 mL chlorobenzene and sulfuryl chloride (48.7 g, 29 mL, 0.35 mole) are added simultaneously over a period of 30 minutes while a stream of gaseous sulfur dioxide and hydrochloric acid is generated rapidly and passed into an alkaline solution. The mixture is heated at 90° C. for 4 hours and any low boilers formed are distilled off. The mixture is cooled to 15° C. with an ice-water bath and the product, p-(chloromethyl)benzoic acid, is collected by filtration, washed with cold (15° C.) toluene (4×25 mL) and dried in a 60° C. vacuum oven. The yield of product is 26.0 g (76% of theory) having a purity of 95% as determined by gas chromatography.

STEP (2)

A mixture of p-(chloromethyl)benzoic acid (24.0 g, 0.14 mole) and triethyl phosphite (95 g, 98 mL, 0.56 mole) is heated at 170° C. (base temperature) for 6 hours in a 250-mL, 3-neck flask. The excess triethyl phosphite and byproducts are distilled off under reduced pressure (approximately 150 torr) and less than 100° C. (base temperature) over a period of about 1 hour. The reaction mixture then is cooled, toluene (100 mL) is added and the toluene solution of the product is washed with water (6×100 mL) to a pH of 4 to 5. The toluene is distilled off under reduced pressure (150 torr) and a temperature of less than 100° C. (base temperature) over a period about 1 hour. The product, consisting primarily of diethyl p-(ethoxycarbonyl)benzylphosphonate, is obtained in a yield of 37 g (88% of theory) and used in step (3) without further purification.

STEP (3)

A slurry of sodium methoxide (10.4 g, 0.19 mole) in dimethylformamide (DMF, 150 mL) is added slowly over a period of 15 to 20 minutes to a mixture of the phosphonate (37 g, 0.123 mole) from step (2) and methyl p-formylbenzoate (20.2 g, 0.123 mole) in 100 mL DMF while maintaining the mixture at 25° to 35° C. by means of cold water cooling. Stirring of the mixture at 25° C. is continued for 4 hours. Water (200 mL) is added slowly while maintaining the temperature at 25° to 30° C. and then stirring at 25° to 30° C. is continued for 1 hour. The product is collected by filtration, washed with water (5×100 mL) to a pH of 6–7, washed with methanol and then dried. The yield of product is 29.5 g, 80% of theory. FDMS analysis shows that a major portion of the product is the methyl ethyl diester and a minor portion is the dimethyl diester of 4,4'-stilbenedicarboxylic acid.

The invention has been described in detail with particular reference to preferred embodiments thereof, but it will be understood that variations and modifications can be effected within the spirit and scope of the invention.

I claim:

1. Process for the preparation of a dialkyl 4,4'-stilbenedicarboxylate having the formula

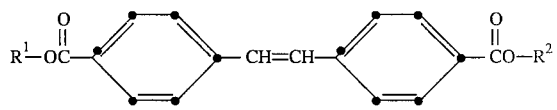

by the steps comprising:

(1) preparing p-(chloromethyl)benzoic acid by chlorinating p-toluic acid with sulfuryl chloride in the presence of a free radical initiator and chlorobenzene or dichlorobenzene;

(2) contacting the p-(chloromethyl)benzoic acid of step (1) with a trialkyl phosphite having the formula $(R^2O)_3P$ to obtain a phosphonate compound having the formula:

(II)

and (1) contacting the phosphonate ester compound of step (3) with an alkyl p-formylbenzoate in the presence of an alkali metal alkoxide and an inert solvent to obtain the dialkyl 4,4'-stilbenedicarboxylate; wherein $R^1$ is alkyl of 1 to 6 carbon atoms and $R^2$ is alkyl of 2 to 6 carbon atoms.

2. Process according to claim 1 wherein step (1) is carried out at a temperature of about 70° to 100° C. using about 1.1 to 2 moles of sulfuryl chloride per mole of toluic acid, a free radical initiator selected from aroyl peroxides and azo compounds, and a solvent selected from chlorobenzene, dichlorobenzene or a mixture thereof in a solvent:p-toluic acid weight ratio in the range of about 1:1 to 5:1.

3. Process according to claim 2 wherein step (2) is carried out at a temperature of about 140° to 180° C. using an amount of trialkyl phosphite which gives a mole ratio of trialkyl phosphite to the p-(chloromethyl)benzoic acid of about 2:1 to 10:1.

4. Process according to claim 3 wherein step (3) comprises using about 1.2 to 2.0 moles alkali metal hydroxide per mole of alkyl p-formylbenzoate, a temperature of about 25° to 35° C., and an inert, polar, aprotic solvent.

5. Process for the preparation of a dialkyl 4,4'-stilbenedicarboxylate having the formula

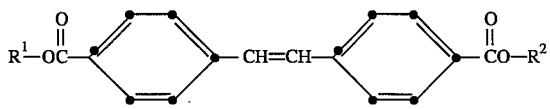

by the steps comprising:

(1) preparing p-(chloromethyl)benzoic acid by chlorinating p-toluic acid with sulfuryl chloride at a temperature of about 70° to 100° C. using about 1.1 to 2 moles of sulfuryl chloride per mole of toluic acid, a free radical initiator selected from aroyl peroxides and azo compounds, and a solvent selected from chlorobenzene, dichlorobenzene or a mixture thereof in a solvent:p-toluic acid weight ratio in the range of about 1:1 to 5:1;

(2) contacting the p-(chloromethyl)benzoic acid of step (1) with triethyl phosphite at a temperature of 140° to 180° C. to obtain a phosphonate compound having the formula:

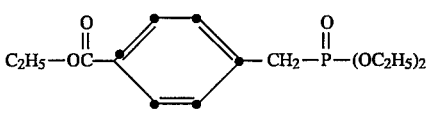

wherein the mole ratio of triethyl phosphite to p-(chloromethyl)benzoic acid is in the range of about 2:1 to 10:1; and (3) contacting the phosphonate ester compound of step (2) with an methyl p-formylbenzoate at a temperature of about 25° to 35° C. in the presence of an alkali metal hydroxide using about 1.2 to 2.0 moles alkali metal hydroxide per mole of methyl p-formylbenzoate and an inert, polar, aprotic solvent to obtain the dialkyl 4,4'-stilbenedicarboxylate;

wherein $R^1$ is methyl and $R^2$ is methyl or ethyl.

6. Process according to claim 5 wherein the free radical initiator used in step (1) is selected from benzoyl peroxide, 2,2'-azobisisobutyrnitrile and 1,1-azobis(cyclohexanecarbonitrile); the triethyl phosphite to p-(chloromethyl)benzoic acid mole ratio is in the range of about 3:1 to 5:1; the alkali metal hydroxide used in step (3) is selected from sodium and potassium alkoxides containing 1 to 4 carbon atoms; and the inert, polar, aprotic solvent used in step (3) is dimethylformamide.

7. Process for the preparation of p-(chloromethyl)benzoic acid which comprises chlorinating p-toluic acid with sulfuryl chloride in the presence of a free radical initiator and in a solvent comprising chlorobenzene, dichlorobenzene, or a mixture thereof.

8. Process according to claim 7 wherein the process is carried out at a temperature of about 70° to 100° C. using about 1.1 to 2 moles of sulfuryl chloride per mole of toluic acid, a free radical initiator selected from aroyl peroxides and azo compounds, and a solvent selected from chlorobenzene, dichlorobenzene or a mixture thereof in a solvent:p-toluic acid weight ratio in the range of about 1:1 to 5:1.

9. Process according to claim 8 wherein the free radical initiator is selected from benzoyl peroxide, 2,2'-azobisisobutyrnitrile and 1,1-azobis(cyclohexanecarbonitrile) and the solvent:p-toluic acid weight ratio is in the range of about 2:1 to 4:1.

* * * * *